(12) United States Patent  
Yang et al.

(10) Patent No.: US 7,652,185 B2  
(45) Date of Patent: Jan. 26, 2010

(54) CATALYST RECOVERY PROCESS

(75) Inventors: Norman Yang, Westfield, NJ (US); Shakeel Tirmizi, Matawan, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 474 days.

(21) Appl. No.: 10/565,143

(22) PCT Filed: Aug. 17, 2004

(86) PCT No.: PCT/US2004/026632

§ 371 (c)(1), (2), (4) Date: Jan. 19, 2006

(87) PCT Pub. No.: WO2005/023419

PCT Pub. Date: Mar. 17, 2005

(65) Prior Publication Data

US 2006/0178545 A1    Aug. 10, 2006

Related U.S. Application Data

(60) Provisional application No. 60/499,764, filed on Sep. 3, 2003.

(51) Int. Cl.
*C07C 2/02* (2006.01)
*C07C 7/00* (2006.01)

(52) U.S. Cl. .................. 585/525; 585/504; 585/521; 585/800; 585/904

(58) Field of Classification Search .......... 585/504, 585/521, 525, 800, 904
See application file for complete search history.

(56) References Cited

U.S. PATENT DOCUMENTS

| 4,263,467 A | 4/1981 | Madgavkar et al. ......... 585/525 |
| 5,254,784 A | 10/1993 | Nurminen et al. ............ 585/525 |
| 5,767,334 A * | 6/1998 | Nissfolk et al. ............. 585/525 |
| 6,075,174 A * | 6/2000 | Presedo ..................... 585/525 |

FOREIGN PATENT DOCUMENTS

EP    0742191    7/1999

* cited by examiner

*Primary Examiner*—In Suk Bullock
(74) *Attorney, Agent, or Firm*—Nancy T. Krawczyk; Andrew B. Griffis

(57) ABSTRACT

A process for reducing boron trifluoride usage and emissions associated with PAO manufacture, the process comprising distilling a portion of the crude PAO product containing a boron trifluoride-organic catalyst at a temperature sufficient to cause the boron trifluoride-organic catalyst to dissociate to produce an overhead stream comprising uncomplexed boron trifluoride and an uncomplexed organic catalyst component, contacting the uncomplexed boron trifluoride and uncomplexed organic catalyst component in a condenser column having an internal structure that increases the recombination of the uncomplexed boron trifluoride and uncomplexed organic catalyst component to form a recycle boron trifluoride-organic catalyst.

14 Claims, 3 Drawing Sheets

US 7,652,185 B2

CATALYST RECOVERY PROCESS

CROSS REFERENCE TO RELATED APPLICATIONS

This application claims the benefit of Provisional Application No. 60/499,764 filed Sep. 3, 2003 and PCT Application No. PCT/US2004/026632, filed Aug. 17, 2004, the disclosures of which are incorporated by reference.

FIELD OF THE INVENTION

The present invention relates to the recovery of catalysts used in the oligomerization of linear alpha olefins to form poly alpha olefins (PAOs). More particularly, the present invention relates to improved recovery of boron trifluoride ($BF_3$) and $BF_3$-organic complex catalysts.

BACKGROUND

PAOs are typically produced by oligomerization of linear alpha olefins in the presence of boron trifluoride and a boron trifluoride-organic catalyst complex. The linear alpha olefins typically have carbon numbers ranging from about 6 to about 16. Typically, alpha-octene, alpha-decene, and alpha-dodecene are used either individually or as mixtures. The organic component of the boron trifluoride-organic catalyst complex comprise alcohols, acetates, acids or ethers having carbon numbers ranging from about 1 to about 10. These organic components are either used individually or as mixtures thereof. Typically, the organic component comprises ethanol, propanol, butanol, pentanol, the corresponding acetates and mixtures thereof. For example, boron trifluoride-butanol/butyl acetate is a catalyst complex.

Boron trifluoride constitutes a significant portion of the manufacturing raw material cost. As a result, it is desirable to minimize the overall usage of boron trifluoride by recycling the boron trifluoride-organic catalyst complex. Moreover, any boron trifluoride that is not recycled is eventually lost to the effluent system. It is desirable to reduce this form of boron and fluorine emissions.

Recycling the boron trifluoride-organic catalyst complex typically involves distilling the boron trifluoride from the crude PAO oligomer reaction mass under a vacuum. However, under the conditions of pressure and temperature in the distillation column, generally at least a portion the boron trifluoride-organic catalyst complex dissociates into boron trifluoride and the corresponding organic constituent(s). Under typical distillation conditions, due to poor contacting of boron trifluoride and the organic constituents, the resulting condensed boron trifluoride-organic catalyst complex is unsaturated. A boron trifluoride-organic catalyst complex is unsaturated when the molar ratio of the sum of the organic component, i.e., alcohols, acetates, acids and/or ethers, to boron trifluoride is greater than about 1:1. The complex is saturated when the molar ratio of alcohol to boron trifluoride is about 1:1. This unsaturation results in loss of free boron trifluoride.

Conventional approaches to improving boron trifluoride recovery and increase boron trifluoride-organic catalyst complex saturation by increasing the condenser residence time and also by using chilled water on the condenser are expensive and also not very efficient. There exists a need for an improved method of recovering boron trifluoride efficiently to reduce boron trifluoride usage and boron trifluoride emissions. There exists a need for an improved boron trifluoride recovery that reduces heat-induced degradation of the boron trifluoride-organic catalyst complex.

SUMMARY OF THE INVENTION

An improved method of recovering boron trifluoride efficiently to reduce boron trifluoride usage and boron trifluoride emissions is disclosed. An improved method of boron trifluoride recovery that reduces vacuum and heat-induced degradation of the boron trifluoride-organic catalyst complex is also disclosed.

An additional gas/liquid contacting device is added to the distillation condenser system. Increased gas/liquid contacting after the distillation column condenser to allow the dissociated boron trifluoride and the organic constituents to efficiently recombine results in increasing the saturation of the recovered catalyst, which is recycled, and hence a reduction in the loss of boron trifluoride. Further cooling is also provided to the gas/liquid contacting device in order to remove the latent heat of formation of the boron trifluoride-organic catalyst complex as well the removal of sensible heat to lower its temperature. The lower temperature results in minimizing the degradation of the recovered boron trifluoride-organic catalyst complex.

One advantage of this invention is the overall reduction in boron trifluoride usage. Because the recycled boron trifluoride-organic catalyst complex is saturated, less boron trifluoride is consumed for saturating it in the continuous stirred tank reactor. The overall quality of the recycled boron trifluoride-organic catalyst complex, because of the high saturation, is such that it can be reused in multiple passes before it loses its reactivity and selectivity.

One advantage of this invention is the overall reduction in boron trifluoride usage. Because the recycled boron trifluoride-organic catalyst complex is saturated, less boron trifluoride is consumed for saturating it in the continuous stirred tank reactor. The overall quality of the recycled boron trifluoride-organic catalyst complex because of the high saturation is such that it can be reused in multiple passes before it loses its reactivity and selectivity. Yet another advantage is the significant reduction in boron and fluorine emissions. By associating more boron trifluoride to the boron trifluoride-organic catalyst complex, less of the boron trifluoride is lost to the vacuum system as an effluent.

DETAILED DESCRIPTION OF THE INVENTION

An improved method of recovering boron trifluoride efficiently to reduce boron trifluoride usage and boron trifluoride emissions is described herein. An improved method for boron trifluoride recovery that reduces vacuum and heat-induced degradation of the boron trifluoride-organic catalyst complex is described herein.

Figure 1:
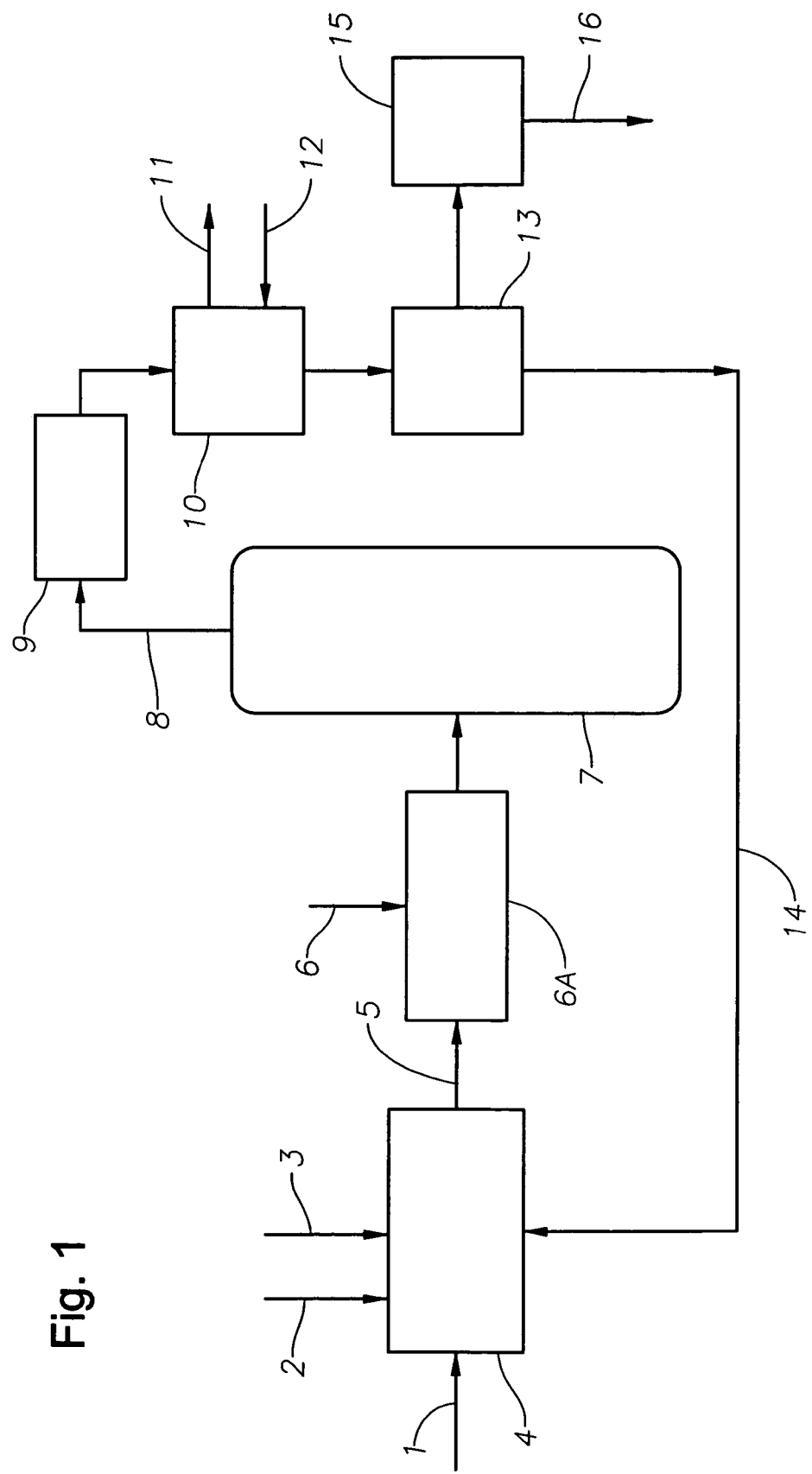
FIG. 1 is a schematic showing one embodiment of an improved catalyst recovery system.

A schematic flow diagram for one embodiment of the invention is illustrated in FIG. 1. Alpha olefin feed 1, preferably consisting of 1-decene or a mixture of octene, decene and dodecene, enters the continuous stirred reactor (CSTR) 4. Fresh boron trifluoride-organic catalyst 2, when needed, as can be readily determined by one of ordinary skill in the art in possession of the present disclosure, recycled boron trifluoride-organic catalyst 14, and boron trifluoride 3 are also fed into the CSTR(s) 4. The crude PAO reaction mass from the CSTR(s) 4 comprising unreacted olefin monomers, dimers and other higher oligomers, boron trifluoride-organic catalyst and boron trifluoride gas is transferred via line 5 and mixed with additional amount of alcohol/acetate feed 6 in injection vessel 6A to associate the free boron trifluoride present in the CSTR(s). This crude PAO reaction mass comprising boron trifluoride-organic catalyst, unreacted alpha-olefin monomer(s) and poly-alpha olefin oligomers is then distilled in a vacuum distillation column 7. The overhead stream taken via line 8 from this distillation column 7 consists of free boron trifluoride, the organic complex that has dissociated from the boron trifluoride-organic catalyst under the conditions of pressure and temperature, and unreacted monomer(s) and dimer(s), which are then partially condensed in the main condenser 9 to form an unsaturated recovered boron trifluoride-organic component complex. This partially condensed mixture, i.e., the unsaturated recovered boron trifluoride-organic component complex, is then brought into further contact in a gas/liquid contactor 10. The efficiency of the gas/liquid contactor 10 may be enhanced by increasing the contact area inside of the gas/liquid contactor 10. By allowing the free boron trifluoride and other constituents to come into contact at a gas/liquid interface, and removing the heat of boron trifluoride-organic catalyst formation by chilled water cooling 11 (exiting) and 12 (entering), the resulting cooled, condensed overhead stream, now a liquid having dissolved boron trifluoride, contains saturated boron trifluoride-organic catalyst, and unreacted monomer. Essentially all, from about 80 wt % to about 100 wt %, of the free boron trifluoride is absorbed to form saturated boron trifluoride-organic catalyst. The condensed, overhead stream enters the phase splitter 13, in which the saturated boron trifluoride-organic catalyst separates, as a bottom phase, from the unreacted monomer(s) and dimer(s) and is recycled back to the CSTR(s) 4 via recycle line 14. Free boron trifluoride, i.e., not complexed as the boron trifluoride-organic catalyst, enters the vacuum system 15 and eventually is discarded as effluent stream 16.

Figure 2A:
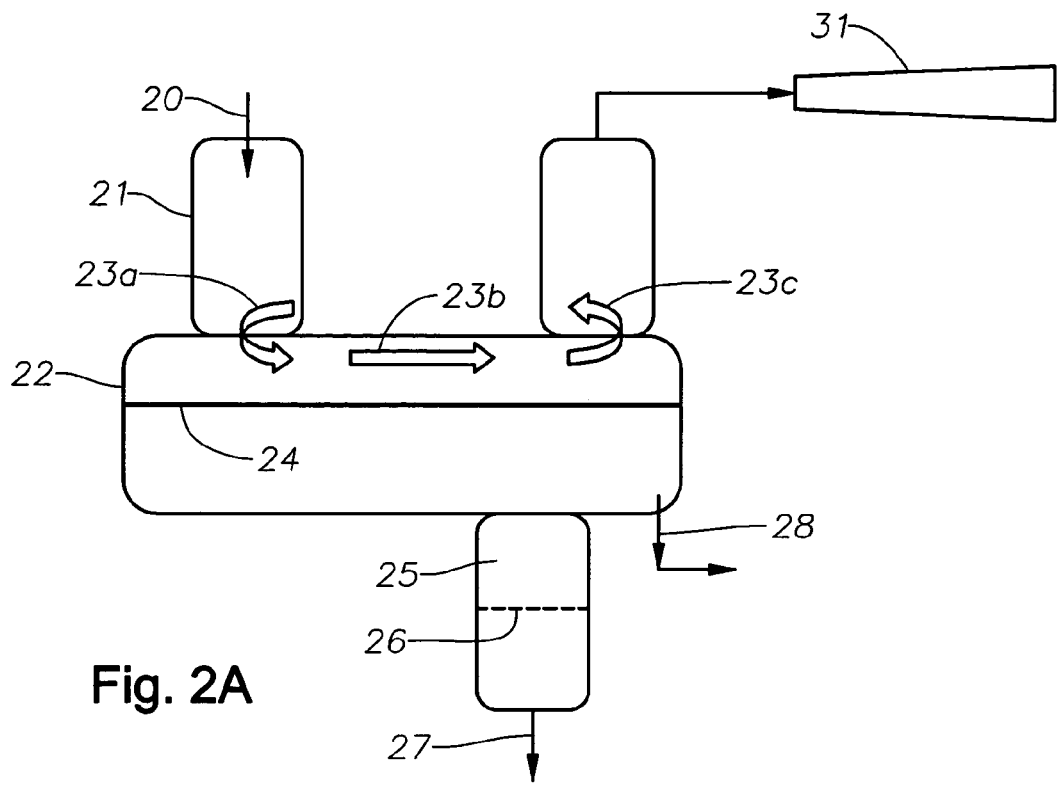
FIG. 2A is a schematic showing one embodiment of a horizontal configuration of a conventional catalyst recovery system.

FIG. 2A shows one embodiment of a conventional horizontal configuration for recombination of the overhead stream from the distillation column (not shown). The overhead stream enters the main condenser 21 via the overhead stream transfer line 20. The condensed overhead stream and any residual vapor enter the accumulator 22. Residual vapor traverses the vapor space as indicated by the outline arrows 23a-c to exit via the steam jets 31 as an effluent. In the accumulator 22, the liquid level 24 is indicated by a solid line. The unsaturated promoter settles in the boot 25. The unsaturated boron trifluoride-organic catalyst is withdrawn via line 27, which may recycle the boron trifluoride-organic catalyst as line 14 in FIG. 1. The accumulator 22 has a monomer and dimer take-off line 28 from which recovered monomer(s) and dimer(s) may be recycled into an alpha olefin feed stream. Uncomplexed boron trifluoride exits as an effluent through the steam jets 31.

Figure 2B:
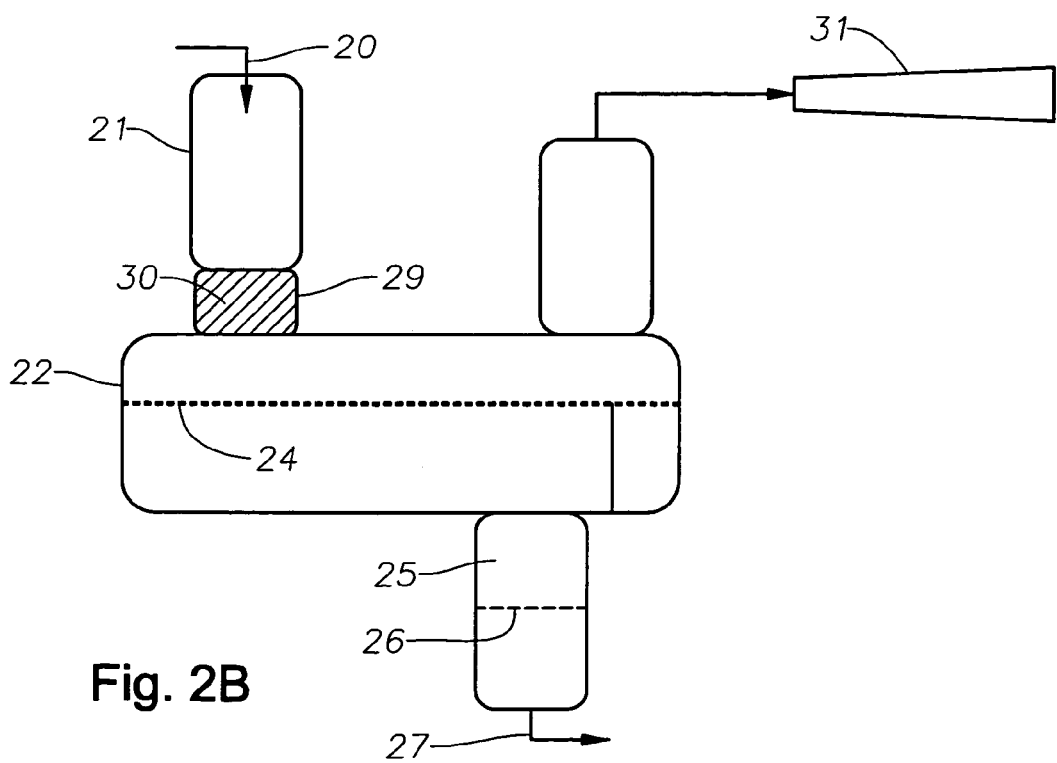
FIG. 2B is a schematic showing one embodiment of a horizontal configuration of an improved catalyst recovery system.

FIG. 2B shows one embodiment of a horizontal configuration of an improved catalyst recovery system. FIG. 2B is similar to FIG. 2A except for the addition of a modified column section 29 between the main condenser 21 and the accumulator 22. The modified column section 29 has an internal structure 30 that is typically a structured packing material, baffles or a combination of a structured packing material and baffles.

Figure 3B:
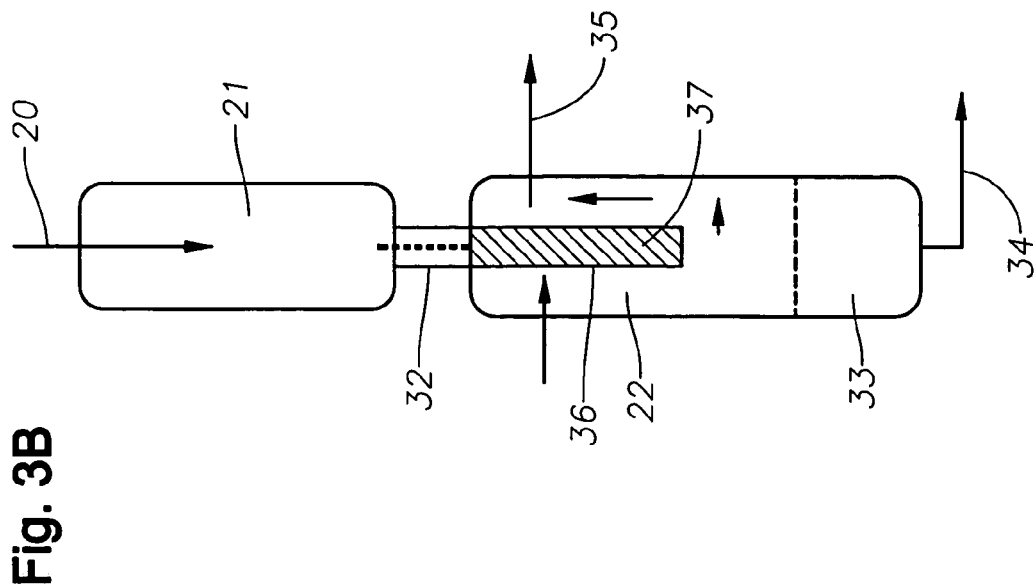
FIG. 3B is a schematic showing one embodiment of a vertical configuration of an improved catalyst recovery system.
Figure 3A:
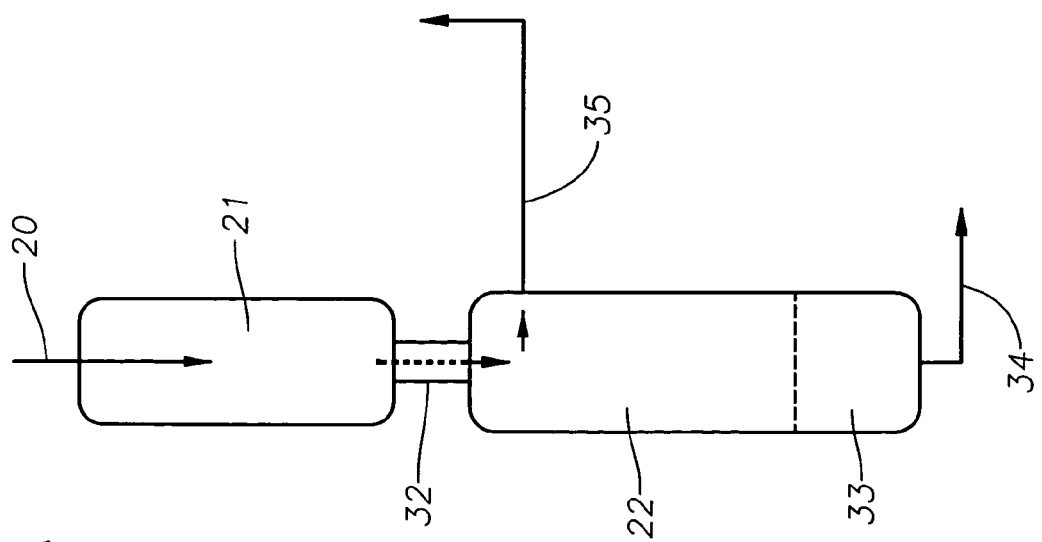
FIG. 3A is a schematic showing one embodiment of a vertical configuration of a conventional catalyst recovery system.

FIG. 3A shows one embodiment of a vertical configuration of a conventional catalyst recovery system. The overhead stream from a distillation column (not shown) enters the main condenser 21 via the overhead stream feed line 20. The condensed overhead stream enters the accumulator via a conduit 32 communicating between the main condenser and the accumulator. The condensed overhead stream comprising monomer and unsaturated boron trifluoride-organic catalyst complex forms a liquid phase 33 in the bottom of the accumulator. The liquid phase 33 is removed from the accumulator 22 by a take-off line 34. Uncomplexed boron trifluoride is drawn through an effluent take-off line 35 into steam jets (not shown).

FIG. 3B shows one embodiment of a vertical configuration of an improved catalyst recovery system. FIG. 3B differs from FIG. 3A by the presence of a modified column section 36. The modified column section 36 has an internal structure 37 that is typically a structured packing material, baffles or a combination of a structured packing material and baffles.

The structured packing material and baffles may be made from any material that is non-reactive under the reaction conditions. Suitable metals include, but are not limited to, stainless steels, Monel, Hastelloy, nickel, and titanium. The structured packing material is typically a high efficiency structured packing material exemplified by Koch-Glitsch wire gauze packing sold under the trademarks FLEXIPAC and GEMPAC; Koch-Glitsch grid structured packing; and Sulzer Bx type packing, sold by Sulzer Chemtech. The surface area of the packing material is typically about 250 $m^2/m^3$, but ranges from about 200 $m^2/m^3$ to about 500 $m^2/m^3$. Packing materials that provide a low pressure drop ranging from about 0.1 to about 0.4 mm Hg/ft of packing are preferred.

One embodiment according to the present invention is a process for the reduction of boron trifluoride emissions from a crude PAO product stream, the process comprising:
  (a) distilling a portion of the crude PAO product comprising a boron trifluoride-organic catalyst at a temperature sufficient to cause the boron trifluoride-organic catalyst to dissociate to produce an overhead stream comprising uncomplexed boron trifluoride and an uncomplexed organic catalyst component,
  (b) contacting the uncomplexed boron trifluoride and uncomplexed organic catalyst component in a condenser column having an internal structure that increases the recombination of the uncomplexed boron trifluoride and uncomplexed organic catalyst component to form a recycle boron trifluoride-organic catalyst, wherein therecycle boron trifluoride-organic catalyst is about 30% greater in saturation than the recycle boron trifluoride-organic catalyst recovered in the absence of the internal structure.

In another embodiment according to the present invention, the process for the reduction of boron trifluoride emissions from a crude PAO product stream comprises distilling a portion of the crude PAO product, comprising a boron trifluoride-organic catalyst and a monomer and/or a dimer of the linear alpha-olefin oligomerized to form the crude PAO product stream, at a temperature sufficient to cause the boron trifluoride-organic catalyst to dissociate to produce an overhead stream comprising uncomplexed boron trifluoride, an uncomplexed organic catalyst component and a monomer of the linear alpha-olefin oligomerized to form the crude PAO product stream, contacting the uncomplexed boron trifluoride, uncomplexed organic catalyst component and the monomer in a condenser column having an internal structure that increases the recombination of the uncomplexed boron trifluoride and uncomplexed organic catalyst component to form a recycle boron trifluoride-organic catalyst, wherein the recycle boron trifluoride-organic catalyst is about 30% greater in saturation than the recycle boron trifluoride-organic catalyst recovered in the absence of the internal structure.

In another embodiment according to the present invention, a process for the reduction of boron trifluoride usage and emissions during the oligomerization of alpha-olefins to form PAOs in the presence of boron trifluoride and a boron trifluoride-organic catalyst complex comprising:
(a) oligomerizing a linear alpha olefin feed mixture by contacting the linear alpha olefin with a mixture comprising fresh boron trifluoride-organic catalyst, recovered boron trifluoride-organic catalyst and boron trifluoride; to form an oligomerization reaction mixture comprising boron trifluoride, boron trifluoride-organic catalyst, unreacted alpha-olefin monomer and poly-alpha olefin oligomers;
(b) complexing the free boron trifluoride by reacting the free boron trifluoride with an organic constituent selected from the group consisting of alcohols, alkyl acetates, alkyl carboxylic acids, ethers and mixtures thereof;
(c) Vacuum distilling the oligomerization reaction mixture at a temperature sufficient to dissociate the boron trifluoride-organic catalyst uncomplexed boron trifluoride and an uncomplexed organic catalyst component;
(d) Contacting the uncomplexed boron trifluoride and uncomplexed organic catalyst component in a condenser column having an internal structure that increases the recombination of the uncomplexed boron trifluoride and uncomplexed organic catalyst component to form a recycle boron trifluoride-organic catalyst, wherein the recycle boron trifluoride-organic catalyst is about 30 % greater in saturation than the recycle boron trifluoride-organic catalyst recovered in the absence of the internal structure.

Another embodiment of the process for the reduction of boron trifluoride usage and emissions, optionally includes the step of removing heat of formation of the boron trifluoride-organic catalyst by cooling a vapor-liquid mixture contacting the internal structure comprising the internal structure, wherein the internal structure comprises a structured packing material, baffles or a combination of a structured packing material and baffles.

Another embodiment of the process for the reduction of boron trifluoride usage and emissions, optionally includes the step of separating the recycle boron trifluoride-organic catalyst from the monomer and/or a dimer olefin overheads of the distillation column. The separation may include any conventional method including, but not limited to, phase separation.

Another embodiment of the process for the reduction of boron trifluoride usage and emissions, optionally includes the step of recycling the recycle boron trifluoride-organic catalyst back into the oligomerization reaction mixture.

The oligomerization reaction can be conducted in a single or multiple stage process to produce a mixture of dimer, trimer, tetramer, and pentamer products. Typically the product of the oligomerization reaction is desirably subjected to fractional distillation and may be blended to form products having 100° C. kinematic viscosity ranging from about 2 to about 10 cSt.

The oligomerized α-olefins of the present invention are preferably subjected to hydrogenation using conventional hydrogenation methodology to reduce at least a portion of the residual unsaturation which remains after the oligomerization. In this regard, typical hydrogenation catalysts such as Pd, Pt, and Ni can be utilized. In the hydrogenation step, it is preferred that at least about 90% of the residual unsaturation be reduced.

The organic catalyst portion of the boron trifluoride-organic catalyst typically comprises an alcohol, an acetate and mixtures thereof. The alcohols typically comprise preferably $C_1$-$C_{10}$ alcohols and more preferably $C_1$-$C_6$ alcohols. The acetates typically comprise preferably $C_1$-$C_{10}$ alkyl acetates and more preferably $C_1$-$C_6$ alkyl acetates.

Boron trifluoride is used as one component of the catalyst in the process of the present invention along with a combination of cocatalysts, i.e., the organic catalyst portion of the boron trifluoride-organic catalyst. When one selects at least one catalyst from the classes of alcohols and at least one selected from alkyl acetates, followed by conventional hydrogenation, a lubricant having a superior balance of properties results. The cocatalyst complexes with the boron trifluoride to form a coordination compound which is catalytically active. In a preferred embodiment, the cocatalyst is used in an amount of from about 0.01 to about 10 weight percent, based on the weight of the α-olefin feed, most preferably about 0.1 to 6 weight percent.

It is preferred that the boron trifluoride be introduced into the reactor simultaneously with cocatalysts and olefin feed. The reaction zone typically contains an excess of boron trifluoride, which is governed by the pressure and partial pressure of the boron trifluoride. Typically, the boron trifluoride is maintained in the reaction zone at a pressure of about 2 to about 500 psig, preferably about 2 to 50 psig. Alternatively, the boron trifluoride can be sparged into the reaction mixture, along with other known methods for introducing the boron trifluoride into the reaction zone.

Suitable temperatures for the reaction are also conventional and can vary from about −20° C. to about 90° C., with a range of about 150 to 70° C. being preferred.

Further details regarding suitable conventional processing methodologies can be found in U.S. Pat. No. 4,045,507, incorporated herein by reference, and in *Synthetic Lubricants and High-Performance Functional Fluids*, Ed. Ronald L. Shubkin, Marcel Dekker, Inc., (New York, 1993).

EXAMPLE 1

A reaction mixture comprising about 10 weight % methyl alcohol, about 23 weight % boron trifluoride and about 67 weight % decene was distilled in a laboratory vacuum distillation column at a pot bottoms pressure of 10 mm Hg and temperature of 220° C. The overheads from this distillation column were condensed in a condenser with cooling water temperature of about 30° C. The recovered boron trifluoride-organic catalyst condensed from the distillation column overheads was about 88 mole % saturated. About 9% of the boron trifluoride dissociated during the distillation was not recovered as evidenced by loss of boron trifluoride through the vacuum system.

EXAMPLE 2

A reaction mixture comprising about 4.7 weight % butyl alcohol, about 2.5 weight % butyl acetate, about 5.8 weight % boron trifluoride and about 87 weight % decene was distilled in a laboratory vacuum distillation column, as described in Example 1, at a pot bottoms pressure of 10 mm Hg and temperature of 220° C. The overheads from this distillation column were condensed in a condenser with cooling water temperature of about 20° C. The boron trifluoride-organic catalyst condensed from the distillation column overheads was about 78 mole % saturated. About 12 mole % of the boron trifluoride dissociated during the distillation was not recovered as evidenced by loss of boron trifluoride through the vacuum system.

EXAMPLE 3

A reaction mixture comprising about 7 weight % butyl alcohol, about 5 weight % butyl acetate, about 9 weight % boron trifluoride and about 79 weight % decene was combined in a laboratory reactor at a system pressure of 2 mm Hg and temperature of about 220° C. The gas vapors from this reactor were condensed in a condenser, as described in Example 1, with the cooling water temperature of about 20° C. Without subjecting the vapors to efficient mixing, i.e, conventional condenser without a structured packing material, the condensed boron trifluoride-butyl alcohol/butyl acetate catalyst was about 65 mole % saturated. About 29 mole % of the boron trifluoride initially present in the reactor dissociates and was not recovered as evidenced by the boron trifluoride lost through the vacuum system.

The same gas vapors when allowed to come into contact via packed elements and baffles resulted in condensed boron trifluoride-butyl alcoholibutyl acetate catalyst that was about 85 mole % saturated. Only about 19 mole % of the total boron trifluoride initially present in the reactor was lost to the vacuum system. Thus there was about a 34 mole % reduction in boron trifluoride lost to the vacuum system compared to the base case with poor vapor/liquid contacting in a conventional condenser. The condenser was a shell and tube condenser having Sulzer BX packing, 3-5 theoretical stages and a residence time of about 15 to about 40 milliseconds.

EXAMPLE 4

A reaction mixture comprising about 20 weight % propanol, about 22 weight % boron trifluoride and about 58 weight % decene was combined in a laboratory reactor at a system pressure of about 2 mm Hg and temperature of about 220° C. The resulting distillation gas vapors were condensed in a condenser, as described in Example 1, with the cooling water temperature of about 20° C. With a conventional column having less efficient mixing, the condensed boron trifluoride-propyl alcohol catalyst was about 61 mole % saturated. About 32 mole % of the boron trifluoride initially present in the reactor dissociated and was not recovered as evidenced by the boron trifluoride lost through the vacuum system.

The same gas vapors when allowed to come into contact via packed elements, as described in Example 3, and baffles, as described in Example 3, resulted in boron trifluoride-propanol catalyst that was about 71 mole % saturated. Only about 18% of the total boron trifluoride initially present in the reactor was dissociated was not recovered as evidenced by boron trifluoride lost through the vacuum system. Thus there was about a 44% reduction in boron trifluoride lost to the vacuum system compared to the base case with poor vapor/liquid contacting in a conventional condenser.

EXAMPLE 5

A reaction mixture comprising about 15 weight % pentanol, about 12 weight % boron trifluoride and about 73 weight % decene was combined in a laboratory reactor at a system pressure of about 2 mm Hg and temperature of about 220° C. The resulting distillation gas vapors from this reactor were condensed in a conventional condenser, as described in Example 1, with the cooling water temperature of about 22° C. With a conventional condenser having less efficient mixing, the condensed boron trifluoride-pentanol catalyst was about 52 mole % saturated. About 23 mole % of the boron trifluoride initially present in the reactor was dissociated and was not recovered as evidenced by the boron trifluoride lost through the vacuum system.

The same gas vapor feed mixture when allowed to come into contact via packed elements, as described in Example 3, and baffles, as described in Example 3, resulted in boron trifluoride-pentanol catalyst that was about 62 mole % saturated. Only about 14% of the total boron trifluoride initially present in the reactor was dissociated as evidenced by the boron trifluoride lost through the vacuum system. Thus, there was about a 39% reduction in boron trifluoride lost to the vacuum system compared to the base case with poor vapor/liquid contacting in the conventional condenser.

While the invention has been described and illustrated with reference to certain preferred embodiments thereof, those skilled in the art will appreciate that various changes, modifications and substitutions can be made therein without departing from the spirit and scope of the invention.

We claim:

1. A process for the reduction of boron trifluoride emissions from a crude PAO product stream, the process comprising the following sequential steps:

oligomerizing a linear alpha olefin feed mixture by contacting the linear alpha olefin with a mixture comprising fresh boron trifluoride-organic catalyst, recovered boron trifluoride-organic catalyst, and boron trifluoride to form an oligomerization reaction mixture comprising free boron trifluoride gas, boron trifluoride-organic catalyst, unreacted alpha-olefin monomer, and poly-alpha olefin oligomers, subsequent to oligomerization, mixing the oligomerization reaction mixture with an organic constituent selected from the group consisting of alcohols, alkyl acetates, alkyl carboxylic acids, ethers and mixtures thereof to yield a crude PAO product of boron trifluoride-organic catalyst, unreacted alpha-olefin monomer, and poly-alpha olefin oligomers, distilling a portion of the crude PAO product at a temperature sufficient to cause the boron trifluoride-organic catalyst to dissociate to produce an overhead stream comprising uncomplexed boron trifluoride and an uncomplexed organic catalyst component, and contacting the uncomplexed boron trifluoride and uncomplexed organic catalyst component in a condenser column having an internal structure that increases the recombination of the uncomplexed boron trifluoride and uncomplexed organic catalyst component to form a recycle boron trifluoride-organic catalyst, wherein the recycle boron trifluoride-organic catalyst is about 30% greater in saturation than the recycle boron trifluoride-organic catalyst recovered in the absence of the internal structure.

2. The process according to claim 1, wherein the internal structure comprises a structured packing material, baffles or a combination of a structured packing material and baffles.

3. The process according to claim 2, wherein the internal structure comprises stainless steels, Monel, Hastelloy, nickel, titanium, plastic, ceramics or mixtures thereof.

4. The process according to claim 1, wherein the loss of boron triflouride ranged from about 25% to about 50% less than the process without the internal structure.

5. The process according to claim 4, wherein the recycle boron trifluoride organic catalyst is from about 52% to about 100% saturated.

6. The process according to claim 1, wherein the organic catalyst comprises an alcohol, an alkyl acetate, an alkyl carboxylic acid, an ether or mixtures thereof.

7. The process according to claim 6, wherein the organic catalyst comprises butyl alcohol, butyl acetate, propanol, pentanol or mixtures thereof.

8. The process according to claim 1, wherein crude PAO product is an oligomeric mixture formed from one or more linear alpha olefins, the linear alpha olefins having from about 6 to about 20 carbon atoms.

9. The process according to claim 8, wherein the one or more linear alpha olefins have from about 8 to about 12 carbon atoms.

10. The process according to claim 1, wherein the overhead stream further comprises the unreacted alpha-olefin monomer; and wherein the contacting step further comprises the monomer.

11. The process according to claim 1, further comprising the step of removing heat of formation of the boron trifluoride-organic catalyst by cooling a vapor-liquid mixture contacting the internal structure comprising the internal structure, wherein the internal structure comprises a structured packing material, baffles or a combination of a structured packing material and baffles.

12. The process according to claim 1, further comprising separating the recycle boron trifluoride-organic catalyst from the monomer and/or a dimer olefin overheads of the distillation column.

13. The process according to claim 12, wherein the separation comprises a phase separation.

14. The process according to claim 1, wherein the temperature sufficient to cause the boron trifluoride-organic catalyst to dissociate is 220° C.

* * * * *

UNITED STATES PATENT AND TRADEMARK OFFICE
CERTIFICATE OF CORRECTION

PATENT NO. : 7,652,185 B2 Page 1 of 1
APPLICATION NO. : 10/565143
DATED : January 26, 2010
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this

Twenty-third Day of November, 2010

David J. Kappos
*Director of the United States Patent and Trademark Office*